United States Patent
Maddela et al.

(10) Patent No.: US 10,591,405 B2
(45) Date of Patent: Mar. 17, 2020

(54) ELECTROCHEMICAL TESTING FOR CORROSION ANALYSIS

(71) Applicant: GM GLOBAL TECHNOLOGY OPERATIONS LLC, Detroit, MI (US)

(72) Inventors: Surender Maddela, Rochester Hills, MI (US); Blair E. Carlson, Ann Arbor, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 318 days.

(21) Appl. No.: 15/584,512

(22) Filed: May 2, 2017

(65) Prior Publication Data

US 2017/0322144 A1 Nov. 9, 2017

Related U.S. Application Data

(60) Provisional application No. 62/331,132, filed on May 3, 2016.

(51) Int. Cl.
| | |
|---|---|
| *G01N 17/02* | (2006.01) |
| *G01N 27/403* | (2006.01) |
| *G01N 27/26* | (2006.01) |
| *G01N 27/28* | (2006.01) |
| *G01N 27/416* | (2006.01) |

(52) U.S. Cl.
CPC ............. *G01N 17/02* (2013.01); *G01N 27/26* (2013.01); *G01N 27/283* (2013.01); *G01N 27/403* (2013.01); *G01N 27/416* (2013.01)

(58) Field of Classification Search
CPC ..... G01N 17/02; G01N 27/283; G01N 27/416
See application file for complete search history.

(56) References Cited

U.S. PATENT DOCUMENTS

| | | | | |
|---|---|---|---|---|
| 5,202,004 A | * | 4/1993 | Kwak | B82Y 35/00 204/400 |
| 5,612,698 A | * | 3/1997 | Reay | H03M 1/181 341/155 |

OTHER PUBLICATIONS

Texas Instrument LMP91000 Datasheet (31 pages), Jan. 2011, revised Dec. 2014 (Year: 2014).*
Kelly et al., "Embeddable Microinstruments for Corrosion Monitoring," Paper No. 294, Corrosion 97, NACE International (Year: 1997).*

(Continued)

*Primary Examiner* — Alexander S Noguerola
(74) *Attorney, Agent, or Firm* — Quinn IP Law

(57) ABSTRACT

A method for testing an electrochemical response of a sample, which is at least partially disposed within an electrolyte, includes macro scanning the sample. Macro scanning is applied across the entire sample and includes applying a first range of macro potential between the electrolyte and the sample, and measuring a first range of macro current between the electrolyte and the sample, while subject to the first range of macro potential. The macro scan is held at a first fixed macro potential within the first range of macro potential and the sample is micro scanned while held at the first fixed macro potential. Micro scanning is applied at individual points across a surface portion of the sample and includes measuring a plurality of first micro currents at each of the individual points of the surface portion of the sample. Each individual point is significantly smaller than the entire sample.

9 Claims, 3 Drawing Sheets

(56) References Cited

OTHER PUBLICATIONS

Díaz-Ballote et al., "Fast-scan cyclic voltammetry-scanning electrochemical microscopy," Journal of Electroanalytical Chemistry 604 (2007) 17-25 (Year: 2007).*

Kwak et al., "Scanning Electrochemical Microscopy V. A Study of the Conductivity of a Polypyrrole Film," J. Electrochem. Soc., vol. 137, No. 5, May 1990 (Year: 1990).*

* cited by examiner

ELECTROCHEMICAL TESTING FOR CORROSION ANALYSIS

CROSS-REFERENCE TO RELATED APPLICATIONS

This application claims the benefit of U.S. Provisional Application No. 62/331,132, filed May 3, 2016, which is hereby incorporated by reference in its entirety.

INTRODUCTION

This disclosure generally relates to electrochemical testing of samples for corrosion analysis thereof. Corrosion, particularly of metals, is an electrochemical process. Therefore, electrochemical techniques may be used to quantify, study, or assess the corrosion of metal articles or to measure the effectiveness of corrosion inhibition techniques.

SUMMARY

A method for testing an electrochemical response of a sample is provided. The sample is at least partially disposed within an electrolyte. The method includes macro scanning the sample, which is applied across the entire sample.

Macro scanning includes applying a first range of macro potential between the electrolyte and the sample, and measuring a first range of macro current between the electrolyte and the sample, while subject to the first range of macro potential. The method also holds the macro scan at a first fixed macro potential within the first range of macro potential.

The method further includes micro scanning the sample, while the sample is being held at the first fixed macro potential. Micro scanning is applied at a plurality of individual points across a surface portion of the sample, such that each individual point is significantly smaller than the entire sample. Micro scanning includes measuring a plurality of first micro currents at each of the individual points of the surface portion of the sample.

The above features and advantages, and other features and advantages, of the present subject matter are readily apparent from the following detailed description of some of the best modes and other embodiments for carrying out the disclosed structures, methods, or both.

DETAILED DESCRIPTION

Figure 1A:
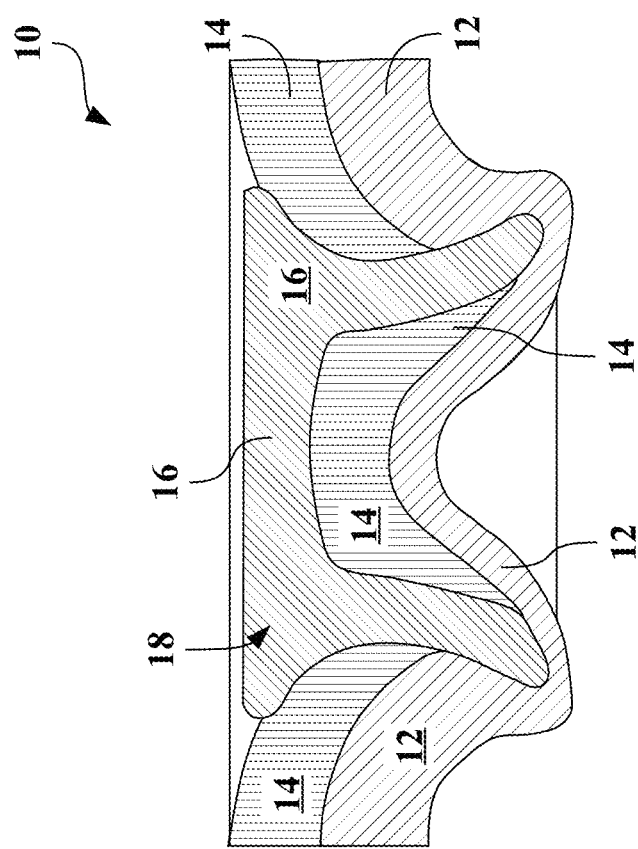
FIG. 1A is a schematic, plan view of a first test sample, illustrated as a self-piercing rivet, having multiple materials interfacing with each other.

In the drawings, like reference numbers correspond to like or similar components whenever possible throughout the several figures. There is shown in FIG. 1A a test sample or sample 10, which may be taken from a larger assembly, the remainder of which is not shown. The sample 10 illustrated in FIG. 1A is a multi-material self-piercing rivet (SPR) joint.

A first material 12, which may be steel, is joined to a second material 14, which may be aluminum or aluminum alloy, by a third material 16, which may be a stainless steel rivet. Portions of each material are in contact with the other two, such that there are numerous dissimilar material interfaces in the sample 10. In preparation for testing, the sample 10 has been cut to expose the interfaces along a face 18, such that the sample 10 may not generally be returned to service. This may be referred to as destructive testing. Portions of the first material 12, the second material 14, and the third material 16 are exposed at the face 18.

Figure 1B:
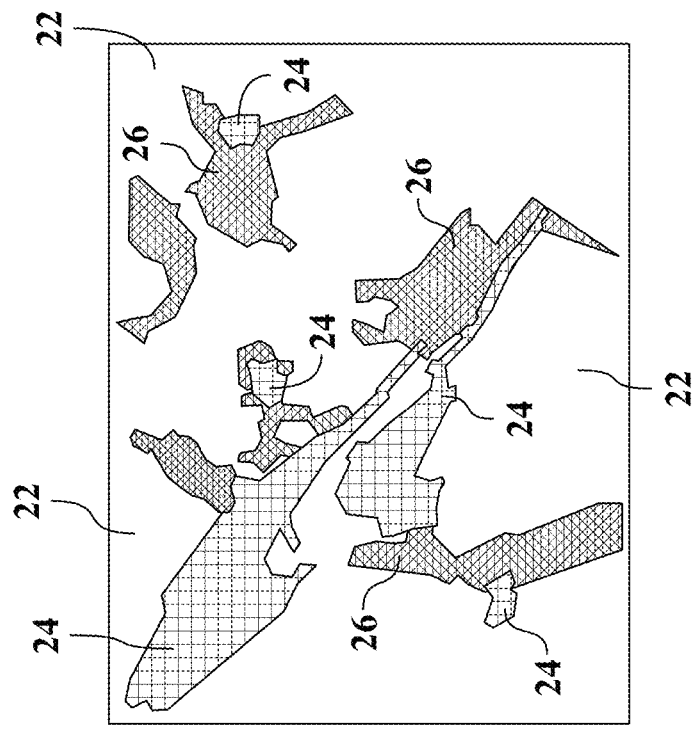
FIG. 1B is a schematic, plan view of a portion of a second test sample, illustrated as a single alloy, having multiple intra-material regions interfacing with each other.

There is shown in FIG. 1B a magnified view of a test sample or sample 20, only a portion of which is shown. The sample 20 illustrated in FIG. 1B is a single alloy, which may be an aluminum alloy. As contrasted with the multi-material sample 10, the sample 20 has only one material. The scale of the view shown in FIG. 1B may be on the order of a few micrometers, while the scale shown in FIG. 1A may be on the order of a few millimeters.

An alloy is generally macro homogenous, such that is treated as a single material on the macro level and appears to the naked eye as a single material. However, the alloy may be micro heterogeneous, as several portions or intra-material regions of different structure may exist. Small regions of the individual elements may be segregated within the final product. Additionally, alloys may have regions of vastly different grain or crystalline structure, such that micro-level interfaces exist between the intra-material regions. Initial manufacturing process and, in particular, heat treatment processes affect both the level of grain differentiation and element segregation within the resulting alloy. For example, and without limitation, a single alloy may have intra-material eutectic portions, matrix portions, or intermetallic portions.

FIG. 1B illustrates at least three different types of intra-material regions. A first region 22 may be a matrix region; a second region 24 may be a eutectic region, and a third region 26 may be an intermetallic region.

While the present disclosure may be described with respect to specific applications or industries, those skilled in the art will recognize the broader applicability of the disclosure. Those having ordinary skill in the art will recognize that terms such as "above," "below," "upward," "downward," et cetera, are used descriptively of the figures, and do not represent limitations on the scope of the disclosure, as defined by the appended claims. Any numerical designations, such as "first" or "second" are illustrative only and are not intended to limit the scope of the disclosure in any way.

Features shown in one figure may be combined with, substituted for, or modified by, features shown in any of the figures. Unless stated otherwise, no features, elements, or limitations are mutually exclusive of any other features, elements, or limitations. Furthermore, no features, elements, or limitations are absolutely required for operation. Any specific configurations shown in the figures are illustrative only and the specific configurations shown are not limiting of the claims or the description.

The sample 10 and the sample 20 shown in FIGS. 1A and 1B may be representative of numerous components used in numerous types vehicles, including planes, trains, automobiles, or any other moving platform. Additionally, industrial, construction, and mining equipment and components may incorporate features of the samples illustrated herein. The testing methodologies described herein may be applied to a broad swath of materials and joints, and the sample 10 and the sample 20 are only examples.

Figure 2:
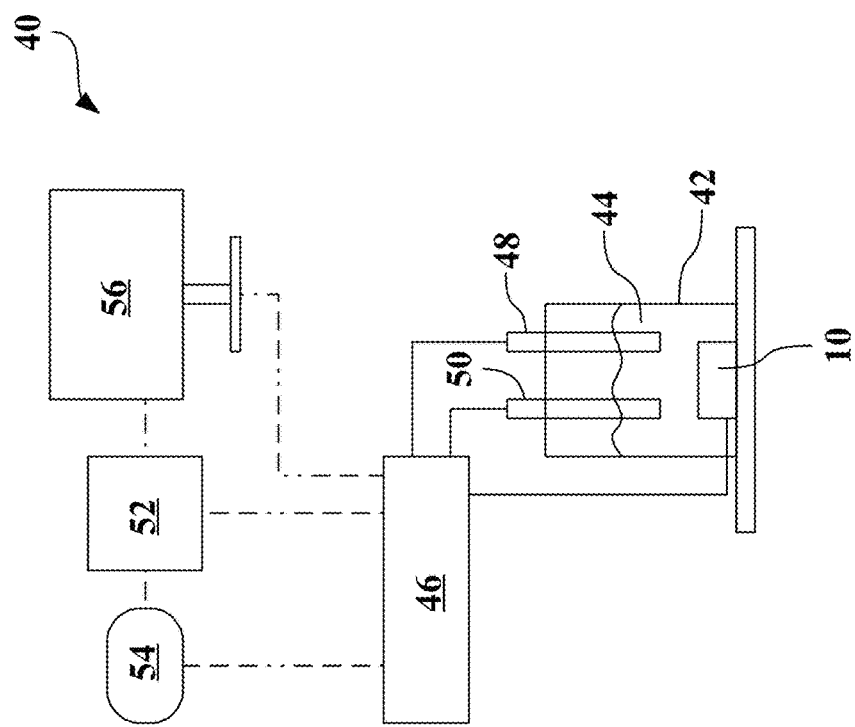
FIG. 2 is a schematic view of a macro test stand for potentiodynamic scanning of samples on a macro level, such as the first test sample or the second test sample shown in FIGS. 1A and 1B.

Referring also to FIG. 2, there is shown a macro test apparatus or macro stand 40, which may be used for testing the electrochemical response of a sample, such as the sample 10 (as shown in FIG. 2) or the sample 20. The macro stand 40 includes a test chamber 42 and an electrolyte 44 disposed within the test chamber 42. The test chamber 42 is generally formed from a non-conductive material.

In the illustrative arrangement shown in FIG. 2, the sample 10 is at least partially disposed within, and may be fully submersed by, the electrolyte 44. The specific type of electrolyte 44 chosen is dependent on the sample 10 and the environment in which the sample 10 is expected to operate. Alternatively, the electrolyte 44 may be selected solely for testing and experimental purposes.

A macro potentiostat 46 is operatively connected to the sample 10 and to the test chamber 42. In particular, the macro potentiostat 46 is in communication with the electrolyte 44 via a reference electrode 48 and a counter electrode 50. Additional structures may support some or all of the components shown and described herein, in addition to others associated with the macro stand 40.

To test the electrochemical response of the sample 10 within the electrolyte 44, the macro potentiostat 46 applies a range of macro potential between the electrolyte 44 and the entire sample 10. More specifically, in the configuration shown, the macro potentiostat 46 varies the potential difference between the sample 10 and the reference electrode 48.

The macro potentiostat 46 also measures a range of macro current between the electrolyte 44 and the entire sample 10 while subject to the range of macro potential. More specifically, in the configuration shown, the macro potentiostat 46 measures the resulting current between the sample 10 and the counter electrode 50. The sample 10 may be referred to as the working electrode for the potentiodynamic scanning executed by the macro potentiostat 46 in the configuration shown.

A controller or control system 52 is configured to operate the macro potentiostat 46 and is in communication therewith. A memory bank 54 is in communication with at least the control system 52. The memory bank 54 is configured to receive and store data regarding the potential applied, and the current measured, by the macro potentiostat 46. In some configurations, the memory bank 54 may be considered a part, or built into the structures, of the control system 52.

A monitor 56 is in communication with at least the control system 52. The monitor 56 is configured to display data related to the potentiodynamic scanning of the sample 10 executed by the macro potentiostat 46. In many configurations, the monitor 56 may display a plot of the applied range of macro current relative to the measured range of macro potential.

The electrochemical response of the sample 10 determined by the macro scan and, in particular, the resulting plot of current-voltage may be instructive as to corrosion capabilities of the entire sample 10. Areas of anodic, cathodic, passive, and transpassive behavior may be identified by skilled artisans in the plot of the applied range of macro current relative to the measured range of macro potential.

The macro scanning applied by the macro potentiostat 46, as illustrated by FIG. 2, is applied across the entire sample 10. Therefore, even though the sample 10 includes three different materials and various interfaces therebetween, the current-voltage plot does not differentiate between the electrochemical behaviors of any of the constituent parts. If the sample were a single, perfectly homogenous, material that resulted in the same current-voltage plot, the corrosion characteristics of the sample would be readily identified. However, with the multi-material sample 10, or with the non-homogenous sample 20, changes in materials or material properties affect the corrosion characteristics.

The control system 52, and other controllers or control systems described herein, is representative of the entire control and computational architecture of the macro stand 40. The control system 52 includes a sufficient amount of memory and processing power to receive signal inputs from, and output commands, data, or instructions to, all systems over which the control system 52 is in command or monitoring.

The control system 52 is an electronic device that is configured, i.e., constructed and programmed, to regulate systems and components of the macro stand 40 and, possibly, any other systems or components associated therewith. The control system 52 may be configured as a central processing unit (CPU). The control system 52 includes a memory, at least some of which is tangible and non-transitory, such as the memory bank 54. The memory available to the control system 52 may be any recordable medium that participates in providing computer-readable data or process instructions. Such a medium may take many forms, including but not limited to non-volatile media and volatile media.

Non-volatile media for the control system 52 and the memory bank 54 may include, for example, optical or magnetic disks and other persistent memory. Volatile media may include, for example, dynamic random access memory (DRAM), which may constitute a main memory. Such instructions may be transmitted by one or more transmission mechanisms, including coaxial cables, copper wire and fiber optics, including the wires that comprise a system bus coupled to a processor of a computer, or wireless communication protocols. Memory of the control system 52 may also include a floppy disk, a flexible disk, hard disk, magnetic tape, any other magnetic medium, a CD-ROM, DVD, any other optical medium, etc.

The control system 52 can be configured or equipped with other required computational hardware, such as a high-speed clock; requisite Analog-to-Digital (A/D) and Digital-to-Analog (D/A) circuitry; input output circuitry and devices (I/O); as well as appropriate signal conditioning and buffer circuitry. Any algorithms required by the control system 52, or accessible thereto, may be stored in the memory and automatically executed to provide the required functionality. The control system 52 may include a plurality of sensors (not shown) for monitoring operation of the macro stand 40.

Figure 3:
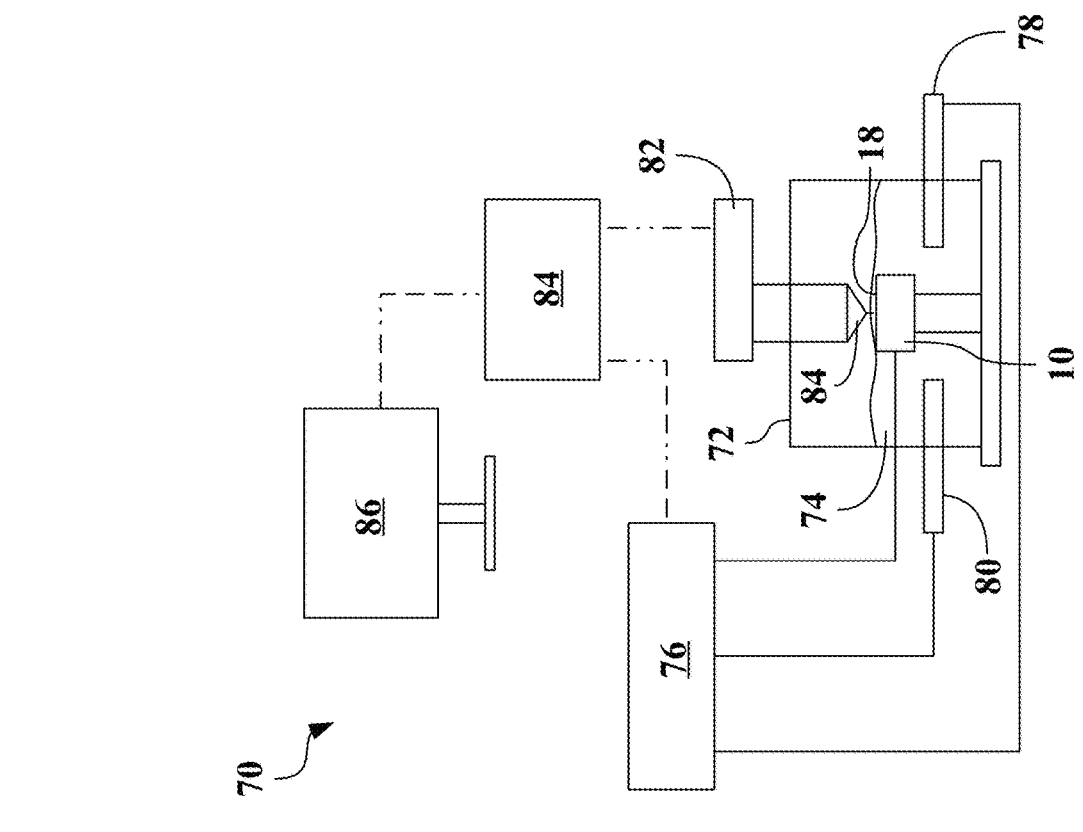
FIG. 3 is a schematic view of a micro-macro test stand for potentiodynamic scanning of samples on both a macro level and micro level, such as the first test sample or the second test sample shown in FIGS. 1A and 1B.

Referring also to FIG. 3, there is shown a micro-macro test apparatus or micro-macro stand 70, which may be used for testing the electrochemical response of a sample, such as the sample 10 (as shown in FIG. 3) or the sample 20. The micro-macro stand 70 includes a test chamber 72 and an electrolyte 74 disposed within the test chamber 72.

In the illustrative arrangement shown in FIG. 3, the sample 10 is at least partially disposed within the electrolyte 74. A macro potentiostat 76 is operatively connected to the sample 10 and to the test chamber 72. In particular, the macro potentiostat 76 is in communication with the electrolyte 74 via a reference electrode 78 and a counter electrode 80. Additional structures may support some or all of the components shown and described herein, in addition to others associated with the micro-macro stand 70.

A micro potentiostat 82 is movably disposed relative to at least one surface portion of the sample 10. In the particular configuration shown, the micro potentiostat 82 is able to sweep across a large portion of the sectioned sample 10 viewable in FIG. 1A.

A controller or control system 84 is configured to operate the macro potentiostat 76 and the micro potentiostat 82, and is in communication therewith. The controller includes sufficient memory, such as within a memory bank that is configured to receive and store data from the macro potentiostat 76 and the micro potentiostat 82.

A monitor 86 is in communication with at least the control system 84. The monitor 86 is configured to display data related to the potentiodynamic scanning of the sample 10 executed by the macro potentiostat 76 and the micro potentiostat 82, as described herein. The micro-macro stand 70 provides an in-situ measurement that is used for prediction and analysis of in-situ corrosion of complex systems, such as those in the multi-material sample 10 or the single alloy sample 20.

Figure 4:
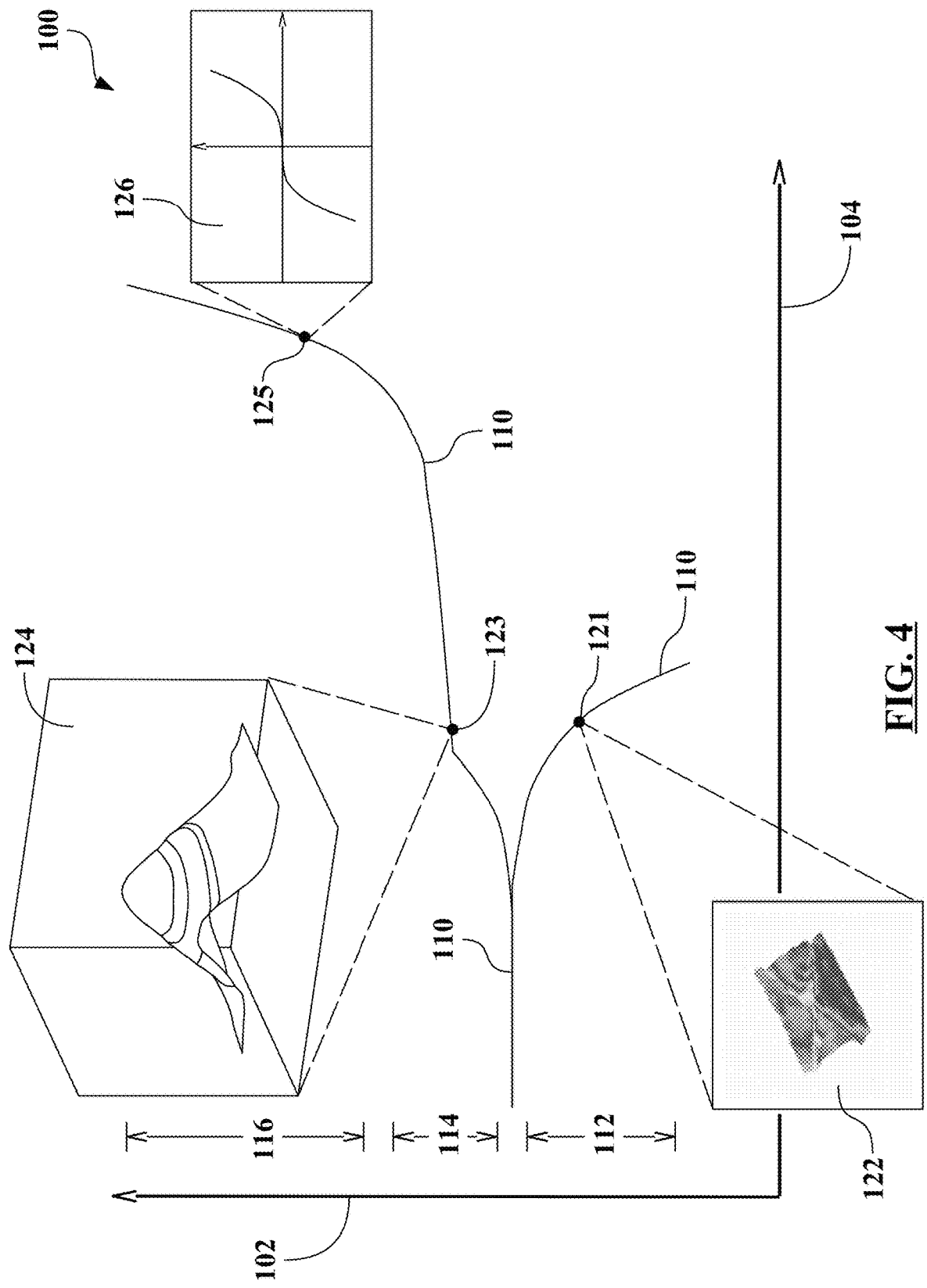
FIG. 4 is a schematic chart illustrating output, which may be displayed on a monitor, printed, or stored, of potentiodynamic scanning with a micro-macro test stand, such as that shown in FIG. 3.

Referring also to FIG. 4, and with continued reference to FIG. 3 and the other figures, there is shown a chart 100, which illustrates output data from potentiodynamic scanning of the sample 10 on the micro-macro stand 70. The chart 100 may be displayed on a monitor 86, printed, or stored. Potential is shown on a y-axis 102 of the chart 100, and current is shown on an x-axis 104 of the chart 100. The description herein may move between FIG. 4 and FIG. 3 interchangeably.

Depending on the configuration of the micro-macro stand 70, the units may vary. However, the potential along the y-axis 102 may be in volts (V) and the current along the x-axis may be in amps (A). Alternatively, the x-axis 104 may be the log of current or current density ($A/cm^2$).

A plurality of current-voltage curves 110 are displayed on the chart 100. These curves represent macro ranges, which may be substantially continuous when applied by the micro-macro stand 70, of potentiodynamic scanning executed by the macro potentiostat 76. Note that the current-voltage curves 110 are also representative of the data output by the macro potentiostat 46 of the macro stand 40 shown in FIG. 2. An approximate location of a first range 112, a second range 114, and a third range 116 of applied potential are also illustrated on the chart 100.

To test the macro-level electrochemical response of the sample 10 within the electrolyte 74, the micro-macro stand 70 is configured for macro scanning of the sample 10. Macro scanning is applied across the entire sample 10, as discussed relative to FIG. 2.

For the macro scan, the macro potentiostat 76 applies the first range 112 (as illustrated in FIG. 4) of macro potential between the electrolyte 74 and the entire sample 10. The macro potentiostat 76 also measures a first range of macro current between the electrolyte 74 and the entire sample while subject to the first range 112 of macro potential.

More specifically, in the configuration shown, the macro potentiostat 76 varies the potential difference between the sample 10 and the reference electrode 78 and measures the resulting current between the sample 10 and the counter electrode 80. The sample 10 may be referred to as the working electrode for the potentiodynamic scanning executed by the macro potentiostat 76, and also by the micro potentiostat 82 in the configuration shown.

The output of the macro scan is illustrated as a two-dimensional potential-current or current-voltage plot. The control system 84 captures the resulting current-voltage data from the macro scan. The control system 84 may plot the measured first range of macro current relative to the applied first range 112 of macro potential.

As shown in FIG. 4, the plurality of current-voltage curves 110 displayed on the chart 100 include portions representing the current measured during application of the first range 112 of macro potential. Note that the data represented on the chart 100 may be displayed on the monitor 86, printed to paper or other tangible media, or transferred to other computational components, such as cloud based resources, for storage or further processing.

The macro potentiostat 76 is configured to hold at a first fixed macro potential 121 within the first range of macro potential. The micro-macro stand 70 is also configured for micro scanning the sample 10 with the micro potentiostat 82 while held at the first fixed macro potential 121 by the macro potentiostat 76. As used herein, the holding at fixed macro potential refers to maintaining the potential at substantially the same levels. However, those having ordinary skill in the art would recognize that, for example, equipment and power supply variations may prevent perfect application of the exact same potential during the holding period, such that variations may occur.

Micro scanning is applied at a plurality of individual points across a surface portion of the sample 10, such that each individual point is significantly smaller than the entire sample 10. The micro potentiostat 82 moves (such as in a sweeping or oscillating fashion) across the surface portion of the sample 10 and measures a plurality of first micro currents at each of the individual points of the surface portion of the sample 10.

The output of the micro scan includes the measured first micro currents relative to the individual points of the surface portion of the sample 10 while held at the first fixed macro potential 121 by the macro potentiostat 76. The control system 84 may plot the measured first micro currents relative to the individual points of the surface portion of the sample 10 to a first micro graph 122, as shown in FIG. 4.

The micro scan plots illustrated as pop-outs in FIG. 4 are plots of the current or current density at the specific surface locations, such that the current may be displayed in one, two, or three dimensions (as illustrated in FIG. 4), with color variations, or with other display and analysis techniques. Note that the data output from the micro scan can also be placed into a table or database, upon which further analysis may be conducted, including algorithms to identify locations of potential corrosion problems or to develop equations representative of the electrochemical response of the surface while held at the first fixed point.

After recording, and possibly plotting, the micro scan results while held at the first fixed macro potential 121, the macro potentiostat 76 may progress to applying the second range 114 of macro potential between the electrolyte 74 and the sample 10. The control system 84 measures a second range of macro current between the electrolyte 74 and the sample 10 while subject to the second range 114 of macro potential, as illustrated in FIG. 4.

The macro potentiostat 76 may be holding the macro scan at a second fixed macro potential 123 within the second range 114 of macro potential. The micro potentiostat 82 then measures a plurality of second micro currents at each of the individual points of the surface portion of the sample 10 while held at the second fixed macro potential 123.

The control system 84 may plot the measured second micro currents relative to the individual points of the surface portion of the sample 10 to a second micro graph 124, as shown in FIG. 4. The first micro graph 122 and the second micro graph 124 are illustrated in FIG. 4 as pop-out or detail portions of the chart 100. However, these may be separate graphs displayed by accessing additional screens on the monitor 86 or different programs within the control system 84.

Furthermore, note that plotting the measured second range of macro current relative to the applied second range 114 of macro potential is displayed by the current-voltage curves 110. The third range 116 of macro potential is also displayed by the current-voltage curves 110. The chart 100 also illustrates a third fixed macro potential 125 at which a third micro graph 126 is developed via micro scanning with the micro potentiostat 82. Note that the first micro graph 122, the second micro graph 124, and the third micro graph 126 are illustrated ion FIG. 4 by different types of plots. However, in many configurations, the same plot or graph type may be used for each of the three micro-scan outputs.

The information gained from the output of the micro-macro stand 70 may be used to better identify, or predict, the actual causes of corrosion within tested samples, such as the sample 10 or the sample 20. The micro scan identifies detailed areas that are responding differently to the fixed macro scan levels. This brings a level of precision and knowledge that is not available with macro scans. In turn, knowledge about the micro level response of the sample 10 and the sample 20 may be used to improve the design, manufacture, or processing of the sample 10 and sample 20.

For example, with the multi-material sample 10, the first micro graph 122 produced by the micro-macro stand 70 may identify that the interface between the first material 12 and the third material 16 has high current flow during the applied first range 112 of macro potential, but that the interface between the first material 12 and the third material 16 is not having the same effects in other situations, such as those shown by the second micro graph 124. Similar macro-micro effects may occur due to the intra-material differences in the single alloy sample 20. For example, the second micro graph 124 produced by the micro-macro stand 70 may identify areas of interests at the intra-material interface between the eutectic second region 24 and the intermetallic third region 26.

The methods and equipment described herein are unique in their ability to measure simultaneous macro and micro galvanic corrosion of a first material/phase relative to a second material/phase, or third material/phase, embedded all within the same joint/matrix. The methods and equipment allow micro potential scanning in conjunction with macro potential measurements for in-situ analysis of galvanic corrosion over the full range of potential.

The detailed description and the drawings or figures are supportive and descriptive of the subject matter discussed herein. While some of the best modes and other embodiments for have been described in detail, various alternative designs, configurations, and embodiments exist.

The invention claimed is:

1. A test stand for testing electrochemical response of a sample, comprising:
   a test chamber;
   an electrolyte disposed within the test chamber, wherein the sample is configured to be at least partially disposed within the electrolyte;
   a macro potentiostat, operatively connected to the sample and the electrolyte, and configured to:
      apply a first range of macro potential between the electrolyte and the entire sample, and measure a first range of macro current between the electrolyte and the entire sample, while subject to the first range of macro potential, wherein applying the first range of macro potential includes sweeping continuously through the first range;
      hold at a first fixed macro potential within the first range of macro potential;
      apply a second range of macro potential between the electrolyte and the entire sample, and measure a second range of macro current between the electrolyte and the entire sample, while subject to the second range of macro potential, wherein applying the second range of macro potential includes sweeping continuously through the second range; and
      hold at a second fixed macro potential within the second range of macro potential;
   a micro potentiostat configured to be movably disposed relative to at least one surface portion of the sample, and configured to:
      measure a plurality of first micro currents at a plurality of individual points of the surface portion of the sample, while the macro potentiostat is held at the first fixed macro potential;
      measure a plurality of second micro currents at a plurality of individual points of the surface portion of the sample, while the macro potentiostat is held at the second fixed macro potential; and
   a control system configured to operate the macro potentiostat and the micro potentiostat.

2. The test stand of claim 1, further comprising:
   a memory bank in communication with the control system, wherein the memory bank is configured to receive and store measurements from the macro potentiostat and the micro potentiostat, and to plot the measured first micro currents relative to the individual points of the surface portion of the sample and to plot the measured second micro currents relative to the individual points of the surface portion of the sample.

3. The test stand of claim 2, further comprising:
   a monitor configured to display a plot of the measured first micro currents relative to the individual points of the surface portion and a plot of the measured second micro currents relative to the individual points of the surface portion of the sample.

4. The test stand of claim 3:
   wherein the memory bank is further configured to receive and store:
      the applied first range of macro current and the measured first range of macro potential; and
      the applied second range of macro current and the measured second range of macro potential; and
   wherein the monitor is further configured to display:
      the plot of the measured first range of macro current relative to the applied first range of macro potential; and
      the plot of the measured second range of macro current relative to the applied second range of macro potential.

5. A method for testing an electrochemical response of a sample at least partially disposed within an electrolyte, comprising:
   macro scanning the sample, wherein macro scanning is applied across the entire sample, and includes:

applying a first range of macro potential between the electrolyte and the sample by sweeping the macro potential continuously through the first range; and measuring a first range of macro current between the electrolyte and the sample while subject to the first range of macro potential;

holding the macro scan at a first fixed macro potential within the first range of macro potential; and micro scanning the sample while held at the first fixed macro potential, wherein micro scanning is applied at a plurality of individual points across a surface portion of the sample, such that each individual point is significantly smaller than the entire sample, and includes measuring a plurality of first micro currents at each of the individual points of the surface portion of the sample;

applying a second range of macro potential between the electrolyte and the sample by sweeping the macro potential continuously through the second range;

measuring a second range of macro current between the electrolyte and the sample while subject to the second range of macro potential;

holding the macro scan at a second fixed macro potential within the second range of macro potential; and measuring a plurality of second micro currents at each of the individual points of the surface portion of the sample while held at the second fixed macro potential.

6. The method of claim 5, further comprising:

plotting the measured first micro currents relative to the individual points of the surface portion of the sample; and plotting the measured second micro currents relative to the individual points of the surface portion of the sample.

7. The method of claim 6, further comprising:

plotting the measured first range of macro current relative to the applied first range of macro potential; and plotting the measured second range of macro current relative to the applied second range of macro potential.

8. The method of claim 7, wherein sample includes a first material and a second material, different from the first material, such that there is at least one dissimilar material interface, and wherein the surface portion of the sample subjected to micro scanning includes portions of both the first material and the second material.

9. The method of claim 7, further comprising: wherein the sample is a single alloy having a first intra-material region and a second intra-material region different from the first intra-material region.

* * * * *